United States Patent [19]

Watson

[11] 4,040,912
[45] Aug. 9, 1977

[54] POLYMERIZATION INHIBITOR FOR VINYL AROMATIC COMPOUNDS

[75] Inventor: James M. Watson, Big Spring, Tex.

[73] Assignee: Cosden Technology, Inc., Big Spring, Tex.

[21] Appl. No.: 531,066

[22] Filed: Dec. 9, 1974

[51] Int. Cl.² .......................... B01D 3/34; C07C 7/00
[52] U.S. Cl. .......................................... 203/9; 203/57; 260/666.5; 260/669 A
[58] Field of Search .................... 260/669 A, 666.5; 203/89, 57, 91

[56] References Cited

U.S. PATENT DOCUMENTS

| 2,410,042 | 10/1946 | Bond, Jr. | 260/669 A |
| 2,900,421 | 8/1959 | Kharasch | 203/9 |
| 3,527,822 | 9/1970 | Benson, Jr. | 203/9 |
| 3,647,637 | 3/1972 | Rosenwald | 203/9 |
| 3,763,015 | 10/1973 | Morimoto | 203/9 |
| 3,816,265 | 6/1974 | Daniels | 203/9 |

Primary Examiner—Wilbur L. Bascomb, Jr.

[57] ABSTRACT

Disclosed is a process for the distillation of readily polymerizable vinyl aromatic compounds and a new polymerization inhibitor therefor. The process comprises subjecting a vinyl aromatic compound to distillation conditions in a distillation system and adding to the system the new polymerization inhibitor comprising an adduct of nitric oxide and styrene.

7 Claims, No Drawings

POLYMERIZATION INHIBITOR FOR VINYL AROMATIC COMPOUNDS

BACKGROUND OF THE INVENTION

The present invention relates to a process for the distillation of readily polymerizable vinyl aromatic compounds, and more especially, to a process for the vacuum distillation of styrene, substituted styrene, divinylbenzene and polyvinylbenzenes wherein the amount of said materials polymerized during distillation is reduced over an extended period of time, wherein the material accummulating in the bottom or reboiler area of the distillation apparatus is free of material contaminated with sulfur and wherein the rate of throughput for a given distillation apparatus can be increased over the rate at which such apparatus may be operated in accordance with conventional methods.

It is well known that vinyl aromatic compounds such as monomeric styrene, lower alkylated styrene, e.g., alphamethyl styrene, and divinylbenzene polymerize readily, and furthermore, that the rate of polymerization increases with increasing temperature. Inasmuch as styrene and divinylbenzene produced by common industrial methods contain impurities, these compounds must be subjected to separation and purification processes in order to be suitable for most types of further industrial use. Such separation and purification is generally accomplished by distillation.

In order to prevent polymerization during distillation of vinyl aromatic compounds, various types of known polymerization inhibitors have been employed in connection with prior art distillation processes. For example, common inhibitors useful for inhibiting the polymerization of vinyl aromatics under distillation conditions include 4-tert-butylcatechol (TBC) and hydroquinone. It is preferred, however, to purify vinyl aromatics by using vacuum distillation techniques, whereby these commonly employed inhibitors are rendered unsuitable in view of the fact that they are effective only in the presence of oxygen. The partial pressure of oxygen in a vacuum distillation column is accordingly too low for these conventional inhibitors to be effective. Sulfur is perhaps the polymerization inhibitor most commonly employed to inhibit polymerization of vinyl aromatic compounds during distillation, since sulfur does provide effective inhibition in the absence of oxygen. While sulfur provides a reasonable effective inhibitor, its use in distillation processes results in one very significant disadvantage, namely, there is formed in the reboiler bottoms of the distillation column a valueless waste material which is highly contaminated with sulfur. This waste material furthermore represents a significant pollution or waste removal problem.

Although many compounds are effective for inhibiting the polymerization of vinyl aromatic compounds under differing conditions, e.g., storage, other purification techniques, etc., for a number of reasons which are not entirely understood in view of the diverse and unpredictable results obtained, only extremely few of these compounds have proved to be of any utility for inhibiting vinyl aromatic polymerization under distillation conditions, particularly under vacuum distillation conditions. In addition, certain compounds which are useful for inhibiting polymerization of one type of vinyl aromatic compound, for example, styrene, have proved to be essentially ineffective for inhibiting polymerization of another species of vinyl aromatic compound, for example, divinylbenzene. A limited number of nitroso compounds have proven to be effective for inhibiting polymerization of styrene monomer during distillation. For example, N-nitroso phenylhydroxylamine and p-nitroso-N,N-dimethylaniline are reasonable effective inhibitors for the distillation of styrene, although they are not particularly soluble in styrene monomer. On the other hand, N-nitroso diphenylamine disclosed in U.S. Pat. No. 3,816,265, assigned to the assignee of the present application has been demonstrated to be a particularly effective polymerization inhibitor under vacuum distillation conditions for both styrene and divinylbenzene, whereas N,N-nitrosomethylaniline as disclosed in U.S. patent application Ser. No. 288, 138, also assigned to the assignee of the present application, has been found to be an excellent polymerization inhibitor for styrene under vacuum distillation conditions. One of the most effective inhibitor systems known for divinylbenzene comprises a mixture of sulfur and N-nitroso phenylhydroxylamine.

In a typical distillation process for vinyl aromatic compounds utilizing a polymerization inhibitor, the mixture of vinyl aromatic to be distilled is generally contacted with the chemical polymerization inhibitor prior to being subjected to distillation conditions in the distillation apparatus. It remains as a significant problem today that the amount of polymer formed in the distillation apparatus and in the high purity product recovered therefrom is substantially higher than desired, and occasionally, that complete polymerization occurs inside of the distillation apparatus. For example, in the process of distilling crude divinylbenzene (a mixture containing divinylbenzenes, diethylbenzenes and monovinylbenzenes) to obtain high purity divinylbenzenes, even when inhibited with sulfur and TBC, a divinylbenzene product is obtained which contains significant quantities of polymer which are difficult to separate from the product and detrimental to the end use of such divinylbenzenes. Furthermore, the material which is removed from the bottom or reboiler area of the distillation apparatus is a highly polluting sulfur-containing waste material which must be disposed of.

It is therefore desirable to provide new polymerization inhibitors which are useful for styrene and vinyl benzenes under distillation conditions, particularly vacuum distillation conditions, and which are not subject to the disadvantages outlined above.

SUMMARY OF THE INVENTION

It is therefore an object of the present invention to provide a new and improved process for the distillation of readily polymerizable vinyl aromatic compounds.

A further object of the invention is to provide a new and improved process for the distillation of readily polymerizable vinyl aromatic compounds, which process results aromatic compound recovery of a high purity unsaturated vinyl aromatic compound and concomitantly in the production of less undesirable by-products.

A further object of the invention resides in the provision of a new and improved process for the distillation of vinyl aromatic compounds which results in the production of substantially less polymerized material in the distillation apparatus.

Yet another object of the invention resides in the provision of a new and improved process for the distillation of vinyl aromatic compounds which avoids the production of a highly polluting, contaminated bottom or reboiler residue.

It is also an object of the present invention to provide a new and improved process for the distillation of vinyl aromatic compounds which permits the distillation apparatus to be operated at an increased rate of throughput without a reduction in efficiency.

It is still a further object of the present invention to provide a new and improved process for the distillation of vinyl aromatic compounds which provides all of the foregoing-enumerated advantages in a vacuum distillation process.

A specific object of the invention resides in the provision of a new and improved polymerization inhibitor for use in the distillation of vinyl aromatic compounds.

In accomplishing the foregoing and other objects, there has been provided in accordance with the present invention a process for the distillation of a readily polymerizable vinyl aromatic compound comprising subjecting the vinyl aromatic compound to distillation conditions in a distillation system in the presence of an adduct of nitric oxide gas (NO) and styrene.

In one aspect of the process according to the invention, the NO-styrene adduct inhibitor is simply introduced into the distillation system by adding it to the reboiler area of the distillation apparatus, or alternatively, by incorporating it into the incoming stream of vinyl aromatic compound to be purified. The amount of NO-styrene adduct necessary to effectively inhibit polymerization of the vinyl aromatic compounds may vary over a wide range depending upon various factors of the distillation process, e.g., temperature, reflux ratio, pressure, residence time, etc. Typically, however, it has been found that an amount of inhibitor between about 200 and about 1000 ppm is sufficient to inhibit polymerization of vinyl aromatic compounds under normal distillation conditions (105° C.).

Through the use of the process according to the present invention, the amount of polymerization occurring within the distillation apparatus is significantly reduced in comparison to conventionally employed methods. In addition, the amount of desired distillation product is increased in proportion to the decrease in the amount of polymer formation. Still further, the material accummulating in the bottom or reboiler area of the distillation apparatus can be reused, e.g., for its fuel valve or for reprocessing, which is a distinct advantage over conventional methods utilizing sulfur as a polymerization inhibitor which produce a highly polluting waste material in the reboiler area. Furthermore, it has also been found that any polymeric material inadvertently formed during the process of the invention is of a low molecular weight character and therefore presents fewer problems in connection with fouling of the distillation apparatus.

There has also been provided in accordance with the present invention a new polymerization inhibitor for vinyl aromatic compounds which comprises the adduct of nitric oxide gas and styrene. The adduct has the chemical formula $C_8H_8N_2O_3$ and is a white crystalline powder having a melting point of approximately 120° C.

Other objects, features and advantages of the invention will become apparent from the detailed description of preferred embodiments which follows.

DETAILED DESCRIPTION OF THE PREFERRED EMBODIMENTS

The distillation process of the present invention employs an adduct of nitric oxide (NO) and styrene as a polymerization inhibitor during the distillation of a vinyl aromatic compound. Typically, the distillation process is carried out under reduced pressure, e.g., vacuum distillation, and one of the significant advantages of the invention is that the use of sulfur in the distillation system can be avoided.

The distillation technique of the process of the present invention is suitable for use in virtually any type of separation of a readily polymerizable vinyl aromatic compound from a mixture wherein the vinyl aromatic compound is subjected to temperatures above room temperature. Surprisingly, the process of the present invention has been found particularly useful in vacuum distillation techniques, the preferred method for separating unstable organic liquid mixtures. In its most useful application, the distillation process of the invention is applied to a distillation mixture containing one of the vinyl aromatic compounds selected from the group consisting of styrene, alpha-methylstyrene, vinyltoluene, vinylnaphthalene, divinylbenzenes and polyvinylbenzenes. The preferred application of the present invention relates to the distillation of crude divinylbenzene or crude styrene under vacuum distillation conditions.

The amount of polymerization inhibitor added may vary over a wide range depending upon the conditions of distillation. Generally, the degree of stabilization is proportional to the amount of inhibitor added. In accordance with the present invention, it has been found that inhibitor concentrations generally between about 50 ppm and about 3000 ppm have generally provided suitable results, depending primarily upon the temperature of the distillation mixture and the degree of inhibition desired.

During vacuum distillation of divinylbenzene-containing mixtures and styrene-containing mixtures, the temperature of the reboiler is preferably maintained from about 150° to about 250° F. by controlling reboiler pressure at from about 30 mm. to about 400 mm. of Hg. Under such conditions, in a distillation apparatus having a distillation zone containing from about 50 to about 100 distillation stages, inhibitor concentrations of from about 100 ppm to about 2000 ppm are suitable, whereas concentrations of from about 100 ppm to about 500 ppm are preferred in the case of styrene distillation and concentrations in the range of from about 200 ppm to about 1000 ppm are preferred for distillation of divinylbenzene. The foregoing ranges are based upon distillation temperatures of from about 150° to 250° F. and residence times of between about 2 and 4 hours. Obviously, in the lower portions of the temperature and residence time ranges, smaller amounts of inhibitor may be utilized. Obviously, amounts of inhibitor greater than those specified hereinabove may be employed, although the advantages of adding the additional inhibitor are not significant and are outweighed by the corresponding increase in cost.

The polymerization inhibitor of the present invention may be introduced into the distillation apparatus in any convenient manner which permits efficient distribution of the inhibitor throughout the apparatus. Typically and most advantageously, the required amount of inhibitor is simply added to the reboiler area of the distillation column, although equivalent results may be obtained by incorporating the inhibitor into the incoming hot stream of vinyl aromatic compound.

Since the inhibitor is gradually depleted during distillation, it is generally necessary to maintain the appropriate amount of inhibitor in the distillation apparatus by adding inhibitor during the course of the distillation process. Such addition may be carried out either on a generally continuous basis or it may consist of intermittent charging of inhibitor into the distillation system. A means by which the maintenance of the necessary inhibitor concentration is carried out is of no particular importance as long as the concentration of inhibitor is kept above the minimum required level.

It has been observed that the inhibitor of the invention decomposes upon heating to its melting temperature to liberate a gas, probably a nitrogen oxide or mixture thereof. The volatility upon decomposition of the inhibitor of the invention results in more effective distribution through the entire length of the distillation apparatus. As a result, polymerization is more effectively inhibited at points in the apparatus remote from the reboiler area than is the case with distillation processes utilizing conventional inhibitors. Also, the need to add inhibitor at numerous points along the distillation column is eliminated.

Another factor enabling the distillation apparatus to operate at an increased rate in accordance with the present invention as opposed to conventional prior art processes is the fact that the inhibitor of the present invention is a more efficient inhibitor at normal temperatures than the conventional inhibitors, and will thus permit higher distillation temperatures and higher pressures. In this way, the rate of distillation can be increased without increasing the amount of polymerization which has been deemed to be acceptable in accordance with conventional distillation procedures.

When the process of the present invention is utilized, the bottoms material which accummulates during the distillation process can be drawn off and utilized for its heating value or for reprocessing. This represents another significant advantage in comparison to conventional processes for vacuum distillation of vinyl aromatic compounds which employ sulfur as the polymerization inhibitor, or sulfur in combination with other chemical polymerization inhibitors. In these conventional processes, a bottoms material is formed which is valueless for further use and constitutes a highly polluting waste material which must be disposed of and which, in this regard, also presents a problem of disposal. Preliminary studies indicate that the bottoms material produced according to the process of the present invention do not possess any unfavorable detonability characteristics.

Upon recovery of the distillation product obtained from the process of the present invention, it is found that a higher percentage of the pure readily polymerizable vinyl aromatic compound is recovered in an unpolymerized state. Furthermore, it has been noted that the polymeric products which are formed during the distillation process of the invention exhibit significantly lower molecular weight characteristics than polymeric products formed in accordance with conventional distillation processes carried out in the presence of the usual inhibitors. This result provides the advantage that there is less fouling in the apparatus and accordingly less chance of plugging. Moreover, the concentrated distillation residues are more easily handled and removed from the apparatus, as by pumping or the like.

The inhibitor of the present invention comprises a white crystalline adduct or complex of nitric oxide and styrene. This adduct is formed upon the addition of nitric oxide to styrene at a temperature between about 0° and 50° C. The preferred process for preparing the adduct comprises bubbling NO gas thru cold styrene at ambient or room temperature. The adduct precipitates from solution and may be recovered by conventional filtration techniques or other conventional techniques, such as centrifugation or the like.

The exact structure of the NO- styrene adduct is not known, although an elemental analysis indicates that the adduct has the following chemical formula: $C_8H_8N_2O_3$. The adduct evidences a melting point of 120° C., and at this temperature it is decomposed to liberate a gaseous product, probably a nitrogen oxide or a mixture thereof.

In order to more fully describe the present invention, the following Examples are presented which are intended to be merely illustrative and not in any sence limitative of the invention.

EXAMPLE 1

100 ml. of styrene at room temperature (25° C) are placed in a 250 ml. flask. Through a tube located below the surface of the styrene NO gas is bubbled slowly through the styrene. A precipitate is observed to form immediately. Gas addition is continued for approximately 15 minutes until a considerable amount of precipitate has formed, and then the gas is shut off and the styrene solution filtered to recover the precipitate. Upon drying the precipitate at 80°-100° C., a white crystalline powder is obtained having a melting point of 120° C. The powder shows an elemental analysis of $C_8H_8N_2O_3$ and decomposes at temperatures above its melting point to liberate a gaseous product.

EXAMPLE 2

50 grams of styrene are placed in a 100 ml. flask, and there is added thereto 0.025 grams (approximately 500 ppm) of the product prepared in Example 1. The flask is sealed with three septums and is purged with nitrogen for 15 minutes using a hypodermic needle at both the inlet and the vent in order to move all dissolved oxygen. The flask and contents are placed in a heated oil both which is thermostatically controlled at 107° C. 1 ml. samples of the styrene are periodically withdrawn from the flask and are mixed with 3 ml. of methanol and examined for cloudiness indicating the presence of polymerized styrene. Samples taken during the first 4 hours of the test show absolutely no clouding whatsoever in the styrene solution, thereby indicating that the inhibitor is extremely efficient. The sample taken at the end of 5 hours of elapsed time shows an opaque reaction and coagulates.

EXAMPLE 3

The procedure of Example 2 is repeated except that divinylbenzene is employed in place of the styrene and the amount of inhibitor employed is .050g. (approximately 1000 ppm). Results equivalent to Example 2 are obtained.

What is claimed is:

1. A process for the distillation of a readily polymerizable vinyl aromatic compound, which comprises subjecting said component to distillation conditions in a distillation system and adding to said system a polymerization inhibitor comprising an adduct of nitric oxide gas and styrene, said adduct of nitric oxide gas and styrene being present in an amount of from about 50 to 3000 ppm based upon the contents of the distillation system, whereby polymerization of the vinyl aromatic compound in the distillation system is substantially inhibited.

2. The process as defined by claim 1, wherein said distillation conditions comprise vacuum distillation conditions.

3. The process as defined by claim 1, wherein said vinyl aromatic compound is styrene.

4. The process as defined by claim 1, wherein said vinyl aromatic compound is divinylbenzene.

5. The process as defined by claim 1, wherein said adduct is the reaction product obtained by contacting nitric oxide gas and styrene at a temperature within the range of from about 0° to about 50° C.

6. The process as defined by claim 1, wherein said polymerization inhibitor is added continuously to said distillation system.

7. The process as defined by claim 1, wherein from about 100 to 2000 ppm of said inhibitor are employed at a reboiler temperature of from about 150° to 250° F. and a reboiler pressure of from about 30 to 400 mm. Hg.

* * * * *